United States Patent [19]

Green

[11] 4,003,789
[45] Jan. 18, 1977

[54] TRIGLYCERIDE-ACCUMULATING CLONAL CELL LINE

[75] Inventor: Howard Green, Brookline, Mass.

[73] Assignee: Massachusetts Institute of Technology, Cambridge, Mass.

[22] Filed: Jan. 8, 1975

[21] Appl. No.: 539,378

Related U.S. Application Data

[62] Division of Ser. No. 438,042, Jan. 30, 1974, Pat. No. 3,884,758.

[52] U.S. Cl. .................................... 195/1.8
[51] Int. Cl.² ................................... C12K 9/00
[58] Field of Search ........................... 195/1.8

[56] References Cited
OTHER PUBLICATIONS

Willmer— Cells and Tissues in Culture, vol. 1, (1965), pp. 167–170. 0
Willmer— Cells and Tissues in Culture, vol. 2, (1965), pp. 287 and

*Primary Examiner*—Sam Rosen
*Attorney, Agent, or Firm*—Arthur A. Smith, Jr.; Martin M. Santa; David E. Brook

[57] ABSTRACT

An isolated clonal cell line derived from the mouse fibroblast 3T3 line is disclosed. This 3T3-L1 clonal cell line has the unique characteristic of accumulating large amounts of triglyceride fats in its resting state, which makes it useful for screening drugs to determine their effect on cell fat accumulation.

3 Claims, No Drawings

TRIGLYCERIDE-ACCUMULATING CLONAL CELL LINE

The invention described herein was made in the course of or under grants from the National Institute of Health.

This is a division, of application Ser. No. 438,042, filed Jan. 30, 1974 now U.S. Pat. No. 3,884,758.

BACKGROUND OF THE INVENTION

1. Field of the Invention

The invention is in the field of biology, and more specifically in the field of cell biology.

2. Description of the Prior Art

Cell lines, as opposed to cell strains, can be serially cultivated indefinitely. Mammalian cell lines have been established, and the more important ones have been deposited with public repositories such as the American Type Culture Collection (ATCC), Rockville, Md.

Established cell lines have been prepared, however, from only a few cell types; for example fibroblasts, epithelial and lymphoid cell lines are known. None of these have the ability to accumulate fats such as triglycerides. Whereas mammalian tissue contains fat-accumulating cells, known as adipose cells, there has heretofore been no known cell line which displayed a similar characteristic.

Because cell lines did not heretofore exist which accumulated fat in a manner similar to naturally occurring adipose cells, it has been difficult to screen drugs for their effects on fat accumulation. Generally, such tests have been carried out using live animals or in vitro using fatty tissues or fatty cells obtained directly from animals. In the former case, it is difficult to accurately and precisely determine such effects, whereas in the latter case the preparations cannot be cultured, only last for a short time, and cannot be used to test drugs for slow or cumulative effects on fat accumulation such as occur in living animals. The number of drugs which can be tested in severely limited by these factors. Further, cell tissue, once removed from an animal, does not always function in a manner similar to the way it functions in the animal. It can be appreciated, therefore, that such screening of drugs has required considerable work, was relatively expensive to carry out, and has not been as accurate and precise as desired.

SUMMARY OF THE INVENTION

In one embodiment, the invention relates to isolated clonal 3T3-L1 cell line, which is derived from cultures of the established mouse fibroblast 3T3 line. A deposit of this new cell line, 3T3-L1, has been made with the American Type Culture Collection (ATCC) and has been assigned number CL 173.

Cultures of the original 3T3 cells contain very small percentages of triglyceride-accumulating cells, and isolation and establishment of a new clonal line from these cells is accomplished by identifying, separating and culturing these cells in a multistage process. The resulting 3T3-L1 clonal cell line can be carried serially in culture for an indefinite period, or kept frozen in the viable state until used. In culture, the clonal line grows until it covers a vessel surface; it then remains in a stable but essentially non-growing state referred to herein as a resting state. In this non-growing state, the clonal line accumulates large amounts of triglyceride fat. This accumulation of triglycerides can normally be detected within a few days and increases for many weeks. At any time, the fatty cells can be observed in the living state under a microscope, or a culture can be fixed and stained with a dye which selectively stains triglyceride fat. The amount of fat can be estimated from the intensity of the selective stain with the naked eye or using a microscope, or the amount can be measured more precisely after extracting the fat with solvent.

When drugs are introduced to a culture medium of resting 3T3-L1 clonal cells, it is possible to observe their effects on the amount of fat accumulated by the cells. Drugs which increase the metabolism of fat and thereby decrease accumulation can be distinguished from drugs which increase fat accumulation or have no appreciable effect. Additionally, drugs can be screened to determine if they block the action of known drugs, such as lipolytic drugs.

Because of this, a simple, economical, reproducible and accurate method is provided for screening drugs to determine their effect on triglyceride fat accumulation. In many cases, the method is also more reliable than previous techniques since the 3T3-L1 cell lines resemble animal or human tissue in the respect that they are, like adipose cells of tissues, stable and non-growing for long periods of time. Drugs possessing properties which affect fat accumulation can be useful in treatment or prevention of obesity, arteriosclerosis, hypertension, or other disorders relating to regulation of fat metabolism.

DESCRIPTION OF PREFERRED EMBODIMENTS OF THE INVENTION

3T3-L1 clonal cell lines described herein are derived from uncloned mouse fibroblast 3T3 cell lines. Like other established lines, the 3T3 line may be propagated indefinitely in serial culture, but unlike most other lines 3T3 cells stop growing when they reach a confluent monolayer and remain viable in a resting state for long periods of time. The 3T3 line was established from disaggregated Swiss mouse embryos and was cultured in Dulbecco-Vogt modification of Eagle's medium containing an approximate four-fold greater concentration of the amino acids (including serine and glycine) and vitamins plus 10% bovine serum. The 3T3 cells were evolved under conditions that favored retention of the property of contact inhibition of cell proliferation and the cells exhibit much more contact inhibition than diploid fibroblasts freshly placed in culture. The 3T3 cell line is described in more detail in: Todaro, G.J. and Green, H., J. Cell Biol. 17:299 (1963). Additionally, a deposit of this line has been made with the American Type Culture Collection and has been assigned ATCC number CCL 92. Further characterization of the 3T3 cell line is given at CCL 92, ATCC, Registry of Animal Cell Lines, Second Edition, 1972.

Isolation of the triglyceride-accumulating clonal cells from 3T3 cells can be done in stages utilizing special techniques. One suitable separation technique is described by Puck, Marcus and Cieciura in "Clonal Growth of Mammalian Cells in Vitro," J. Exptl. Medicine 103:273 (1956), the teachings of which are hereby incorporated by reference. In this method, clones are isolated by removing the medium from the parent cell culture and placing over the clones a sterile stainless steel cylinder (e.g., 6 mm. diameter × 10 mm. high) whose bottom edge is coated with silicone stopcock grease. A small amount of trypsin solution is introduced into the cylinder, and after about 10 minutes at 37° C. the clonal cells are dislodged by gentle pipetting, and inoculated with fresh medium into another culture dish.

Isolation of 3T3-L1 clonal cells begins with identification of fat-rich areas in resting cultures of 3T3 cells. These fat-rich areas only appear when the 3T3 cells are in a resting state, and usually comprise an exceedingly small percentage of a 3T3 colony. Typically, for example, the fat-rich areas might comprise less than about 1% of the cells of the confluent 3T3 monolayer. When the fat-rich cells in these areas are transferred and grown out, fatty cells are usually not seen among the growing progeny, but the proportion of fat-accumulating cells in the resting state is much higher; typically it might comprise about 5% or more after one culture. This separation and culturing process is repeated, and finally, by inoculation at sufficiently low density, colonies possessing fat-accumulating cells can be identified while they are still small enough to be well separated from adjacent colonies.

These isolated 3T3-L1 clones resemble adipose cells in their accumulation of large quantities of triglyceride fats, but the cells are generally not as large, the nucleus remains in a central position and there is more non-fatty cytoplasm. However, some cells accumulate a very large central fat droplet and the surrounding cytoplasm is compressed into a thin rim, as in adipose cells of tissues. The amount of triglyceride fat accumulated in individual 3T3-L1 cells is widely variable but is likely to be orders of magnitude greater than by non-fat-accumulating cell types. For instance, 3T3 fibroblast cells typically accumulate fat to less than 1% of their dry mass, whereas 3T3-L1 clonal cells might accumulate 50%. Because of their fat-accumulating property, these cells are termed "adipose-like" herein, although this should not be construed to mean that they are necessarily derived from the same cells as are the adipose cells of tissues.

Triglyceride fats only appear to be accumulated in significant amounts when 3T3-L1 cells are in a resting condition. When a small number of 3T3-L1 cells are inoculated onto a substrate, they grow until a confluent monolayer is formed, and then enter a resting state. In this respect, 3T3-L1 cells resemble their parent 3T3 line. Suitable substrates include plastic or glass.

A resting state can be achieved almost immediately by inoculating the cells in suspension in a suitable medium such as methyl cellulose, agar, or other suitable medium.

If the 3T3-L1 cells accumulate too much fat, they lose their ability to grow when transferred to culture conditions favoring growth. When cultures having accumulated a great deal of fat are trypsinized and transferred, cells which have accumulated the most fat do not even spread out on the culture vessel. They do survive for many days without change, but eventually usually disintegrate. Less fatty cells spread on the vessel surface and reinitiate a division cycle. In some cases, the division is abortive because of failure of cytokinesis, but usually the divisions seem to take place normally, the fat presumably being diluted in the progeny.

The high fat content of these 3T3-L1 clones contrasted to other cell types presumably indicates that there is either greater fat uptake from the medium, greater synthesis of fat by the cells or reduced degradation of fat. Although the cause of the accumulation has not been conclusively ascertained, it is known that fat accumulation can be significantly reduced by agents with known lipolytic properties such as cyclic AMP, epinephrine, and isoproterenol. Also, drugs which increase the accumulation of fat, have no appreciable effect, or block the action of other fat-regulating drugs can be introduced into the 3T3-L1 cells. Because of this, the effect of any drug or compound on fat accumulation can be determined by contacting resting clonal cells with the drug to be tested. This can be done with the cells suspended in a medium or with the cells in a confluent monolayer on a substrate. Since triglyceride fats are present in the culture medium, or are synthesized by the cells, there is normally no need to provide an external supply of these fats. Appropriate concentrations for each drug will be easily ascertainable by those skilled in the art.

Resting 3T3-L1 cells respond to epinephrine and isoproterenol by decreasing their fat accumulation, presumably due to the adrenergic effect of these drugs. This means that the cell line can be used to screen drugs for adrenergic or antiadrenergic functions, using their effect on fat accumulation as a criterion. Drugs possessing such functions can then be tested in the more complicated traditional systems for effects on cardiac contractility, blood pressure, etc. Thus, 3T3-L1 cell line can be used to screen drugs for adrenergic or antiadrenergic properties, which would make them useful for treatment of diseases such as hypertension, asthma, and cardiac disease.

Other characteristics of the isolated clonal cells have been determined. The clonal cells grow with a doubling time of less than 24 hours, having a plating efficiency of about 20–50%, and a saturation density in surface cultures which is similar to that of 3T3 line (about $5 \times 10^4 /cm^2$.) In regard to karyotypic properties, the majority of 3T3-L1 cells have a mean of 74 acrocentric and telocentric chromosomes. Approximately 24% have double this number.

Fat-accumulating 3T3-L1 cell lines are handled by art recognized techniques. They can be frozen by suspending cultures in dry ice or by other such known techniques; a suitable freezing medium can be made by adding 10% glycerol to the culture medium described infra, although many others would be suitable. Cultivation is accomplished in a medium such as Dulbecco-Vogt modification of Eagle's medium, 90%; bovine serum, 10%; with penicillin and streptomycin being added to prevent bacterial infection. Of course, other art recognized culture media could also be used.

The invention is further specifically illustrated by the following examples.

EXAMPLE 1

Two triglyceride-accumulating clones were isolated from mouse fibroblast 3T3 cell line. This was done in stages, beginning with the isolation of fat-rich areas in confluent resting cultures of parent 3T3 cells. The confluent resting culture of parent cells was formed by inoculating 100,000 3T3 cells in a medium comprising fortified Eagle's medium supplemented with 10% calf serum in a petri dish. The 3T3 cells reached confluence after about 4 days, and small areas containing fat could be identified several days later by ordinary light microscopy. Areas in which the fatty cells were most striking were isolated by removing the medium and placing over each colony a sterile stainless steel cylinder, 6 mm. in diameter × 10 mm. high, whose bottom edge was coated with silicone stopcock grease. A small amount of trypsin solution was introduced into the cylinder and, after about 10 minutes at 37° C., the cells were dislodged by gentle pipetting and inoculated with fresh medium into another culture dish. When the transferred cells were grown out, the proportion of cells accumulating fat in the resting state was much higher. The transfer and growing out steps were repeated and finally, by inoculation at sufficiently low density, i.e., to result in the formation of only a small number of colonies, colonies possessing fatty cells could be identified while they were still well separated from adjacent non-fat-accumulating colonies. The two clones isolated in this manner both had an extraordinary tendency to accumulate fat, and it is believed that both clones were identical.

Fat accumulation was observed by fixing resting monolayers with 1% formalin and staining with Oil Red-0, which is specific for cytoplasmic fat, and optionally with hematoxylin, to stain the nuclei.

One observation was made by inoculation of 100 cells into a petri dish. This culture became confluent about 2 weeks after inoculation, and fat accumulation began in those cells whose growth was first arrested, i.e., the cells in the centers of the colonies. After 6 weeks, the cells were stained and fixed Cells containing heavy amounts of fat were grouped in colonies but the colonies were separated by a confluent sheet of cells which had not yet accumulated appreciable fat.

Another observation was made of a culture inoculated 4 weeks previously with about $10^5$ cells. This culture was viewed under low power and high power magnification and it was noticed that most of the cells were engorged with fat.

Other observations indicated that some of the cultures contained cells in which the accumulation of fat is marked whereas it had not begun in other cells in the same culture. It was also observed that in cells having massive accumulations of fat, nuclear division occurred but cytokinesis seemed to fail and the cell became binucleate. It was further observed that developing clones originating from previously identified single cells with moderately heavy fat deposits eliminated their fat by dilution during growth.

In order to contrast accumulated fat in approximately $10^5$ cells of 3T3 -L1 and 3T3 after both had been in the resting state for about 3 weeks, monolayers of each were trypsinized and the cells were sedimented in a centrifuge. The cell pellets were extracted with methanol: chloroform: water in a ratio of 2:1.0:0.8 according to the method of Kates, M., "In Laboratory Techniques in Biochemistry and Molecular Biology," Vol. 3, T.S. Work and E. Work, eds., Amer. Elsevier Publ. Co., N.Y., Chaps. 3, 4 and 7 (1972). The extracts were subjected to thin layer chromatography on silica gel using petroleum ether: ethyl ether: acetic acid in the ratio 80:20:1, also according to the method of Kates, and the resulting chromatograms were developed with iodine vapor. The chromatogram showed roughly similar amounts of phospholipid and cholesterol in the 3T3-L1 clonal colony and in a colony of parent 3T3 line, but a dark spot corresponding to triglyceride was obtained from the extract of the clonal colony but not from the extract of 3T3 line. A fat with mobility between triglyceride and diglyceride was also obtained only from the fat-accumulating cell line.

EXAMPLE 2

Cultures of triglyceride-accumulating clonal 3T3-L1 cell colonies isolated following the procedures of Example 1 were allowed to grow to confluence and different agents were then added to the medium in relatively high concentration at each feeding which occurred three times daily for 2 weeks. The cells were subsequently observed for fat accumulation over a period of 2 weeks. $N^6$, $O^2$ -dibutyrylcyclic AMP (dbc-AMP) in a concentration of $10^{-3}$ molar greatly reduced the accumulation of fat. L-epinephrine in a concentration of $3 \times 10^{-4}$ molar was also extremely effective, although the effect was less than with dbc-AMP. Another adrenergic agent, isoproternol, added in a concentration of $10^{-4}$ molar was more effective than epinephrine in reducing fat accumulation. These agents did not seem to affect the number of cells that were detectably fatty, but only the amounts of fat those cells accumulated.

There are other equivalents to the specific embodiments of the invention described herein, and these are intended to be covered by the appended claims. For example, although it is known that the 3T3-L1 clonal cells accumulate triglyceride fats, they may also accumulate other lipids or fats in which case they could be used to screen for the effect of drugs on such other lipids or fats. Additionally, it might be possible, using the techniques described herein, to isolate other fat-accumulating clonal sublines, even starting from different parent cell lines, and such clonal adipose-like cell lines could be used to test for the effect of drugs on fat accumulation.

What is claimed is

1. An isolated clonal cell line derived from a culture of mouse fibroblast 3T3 cell line, said clonal cell line having the characteristic of accumulating relatively large amounts of triglyceride fats while in a resting state and a suitable growth media therefrom.

2. A method for isolating and establishing a triglyceride-accumulating clonal cell line from a fibroblast parent cell culture comprising:
   a. separating a portion from said parent culture which is rich in triglyceride-accumulating cells;
   b. transferring said portion to a culture medium;
   c. growing a new culture from said transferred portion;
   d. repeating steps (a) through (c) until a separate colony of triglyceride-accumulating clonal cells is established; and,
   e. separating said colony in a pure state.

3. A cell culture comprising isolated 3T3-L1 cells in a suitable medium therefor.

* * * * *